(12) United States Patent
Vander Meer et al.

(10) Patent No.: US 8,575,328 B2
(45) Date of Patent: Nov. 5, 2013

(54) FORMICIDAE (ANT) CONTROL USING DOUBLE-STRANDED RNA CONSTRUCTS

(75) Inventors: Robert K. Vander Meer, Newberry, FL (US); Man Yeon Choi, Gainesville, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 1 day.

(21) Appl. No.: 13/323,880

(22) Filed: Dec. 13, 2011

(65) Prior Publication Data

US 2012/0148524 A1    Jun. 14, 2012

Related U.S. Application Data (60) Provisional application No. 61/422,721, filed on Dec. 14, 2010.

(51) Int. Cl.
- C07H 21/02 (2006.01)
- C07H 21/04 (2006.01)
- C12Q 1/68 (2006.01)
- C12N 15/63 (2006.01)

(52) U.S. Cl.
USPC ........ 536/24.5; 435/6; 435/91.1; 435/91.31; 435/455; 536/23.1; 536/24.31

(58) Field of Classification Search
USPC .............. 435/6, 91.1, 91.31, 455; 514/44; 536/23.1, 24.5, 24.31
See application file for complete search history.

(56) References Cited

U.S. PATENT DOCUMENTS

2009/0004668 A1*   1/2009   Chen et al. .............. 435/6

FOREIGN PATENT DOCUMENTS

WO    WO 02/44321    *   6/2002

OTHER PUBLICATIONS

Doench et al., Genes & development, vol. 18, No. 5, pp. 504-511 (2004).*
Holen et al., Nucleic Acids Res., vol. 30, No. 8, pp. 1757-1766 (2002).*
Peracchi et al., Rev. Med. Virol., vol. 14, pp. 47-64 (2004).*
Opalinska et al., Nature Rev., vol. 1, pp. 503-514 (2002).*

\* cited by examiner

*Primary Examiner* — Jane Zara
(74) *Attorney, Agent, or Firm* — John Fado; Albert Y. Tsui; Lesley Shaw (57) ABSTRACT

Disclosed is a dsRNA construct that relates to a method to control Formicidae (ants) via double-stranded RNA interference of the PBAN/Pyrokinin gene.

17 Claims, 4 Drawing Sheets

FORMICIDAE (ANT) CONTROL USING DOUBLE-STRANDED RNA CONSTRUCTS

CROSS-REFERENCE TO RELATED APPLICATION

This present application claims priority under 35 U.S.C. §119(e) to U.S. Provisional Ser. No. 61/422,721, which was filed on Dec. 14, 2010, and is hereby incorporated by reference.

FIELD OF THE INVENTION

This invention relates to a method to control *Solenopsis invicta* via double-stranded RNA interference of the PBAN/Pyrokinin gene.

BACKGROUND OF INVENTION

Insect pests cost the general public billions of dollars annually in losses. These losses include the expense of controlling insect pests as well as crop loss and property damage caused by the pests. Specifically ants comprise 5% of the world's hundred worst invasive alien species as reported in Lowe S., Browne M., Boudjelas S., De Poorter M. (2000) 100 of the World's Worst Invasive Alien Species A selection from the Global Invasive Species Database. Published by The Invasive Species Specialist Group (ISSG) a specialist group of the Species Survival Commission (SSC) of the World Conservation Union (IUCN), 12 pp. First published as special lift-out in Aliens 12, Dec. 2000 and electronically available at http://www.issg.org/database/species/search.asp?st=100ss. Of the 17 land invertebrates listed, 28% are ants, including fire ants (*Solenopsis* spp.), Argentine ant (*Linepithema humile*), the little fire ant (*Wasmannia auropunctata*), and the crazy ant (*Paratrechina* spp). All of these ants have substantial economic impact. More specifically, the well-documented fire ant currently infests over 320 million acres in the United States and over $6 billion per year is spent for control and damage repair (as reported in Lard, C. F., J. Schmidt, B. Morris, L. Estes, C. Ryan, and D. Bergquist. 2006. "An economic impact of imported fire ants in the United States of America." Texas A&M University, College Station, Texas. Available online at http://fireantecon.tamu.edu). The economic sectors affected include: residential households, electric and communication systems, agriculture (crops and livestock), golf courses, commercial businesses, schools and medical facilities, and parks and recreational areas.

The red imported fire ant, *Solenopsis invicta* Buren (Hymenoptera: Formicidae), was introduced from Brazil into United States in the 1930's and have been found in many southern and western parts of the United States from Maryland to southern California. The red imported fire ant has become a major agricultural and urban pest throughout those parts of the United States as *S. invicta* can cause significant damage to soybean, citrus, corn, okra, bean, cabbage, cucumber, eggplant, potato, sweet potato, peanut, sorghum, cotton and sunflower. Their mound-building activity can damage plant roots, leading to crop loss as well as interference with mechanical cultivation of crops.

Chemical pesticides are the primary tools used to combat these insect pests. However, use of traditional chemical pesticides has disadvantages, including non-target effects on neutral or beneficial insects, as well as other animals. Chemical pesticide usage also can lead to chemical residue run-off into streams and seepage into water supplies resulting in ecosystem/environment damage. In addition, animals higher in the food chain are at risk when they consume pesticide contaminated crops or insects. The handling and application of chemical pesticides also presents exposure danger to the public and professionals, and could lead to accidental dispersal into unintended environmentally sensitive areas. In addition, prolonged chemical pesticide application may result in an insect population becoming resistance to a chemical pesticide. In order to control a traditionally chemical resistant-pest, new more potent chemical pesticides must be utilized, which in turn will lead to another resistance cycle. As such, there is a need in the art to control pest populations without the disadvantages of traditional chemical pesticides.

An approach to decrease dependence on chemical pesticides is by causing a specific gene(s) of the target-pest to malfunction by either over expression or silencing gene expression. The silencing approach utilizes RNA interference pathways to knockdown the gene of interest via double-stranded RNA. Double strand RNA (dsRNA) induces sequence—specific post-transcriptional gene silencing in many organisms by a process known as RNA interference (RNAi). RNAi is a post-transcriptional, highly conserved process in eukaryotes that leads to specific gene silencing through degradation of the target mRNA. The silencing mechanism is mediated by dsRNA that is homologous in sequence to the gene of interest. The dsRNA is processed into small interfering RNA (siRNA) by an endogenous enzyme called DICER inside the target pest, and the siRNAs are then incorporated into a multi-component RNA-induced silencing complex (RISC), which finds and cleaves the target mRNA. The dsRNA inhibits expression of at least one gene within the target, which exerts a deleterious effect upon the target.

Fire, et al. (U.S. Pat. No. 6,506,559) discloses a process of introducing RNA into a living cell to inhibit gene expression of a target gene in that cell. The RNA has a region with double-stranded structure. Inhibition is sequence-specific in that the nucleotide sequences of the duplex region of the RNA and of a portion of the target gene are identical. Specifically, Fire, et al. (U.S. Pat. No. 6,506,559) discloses a method to inhibit expression of a target gene in a cell, the method comprising introduction of a double-stranded ribonucleic acid into the cell in an amount sufficient to inhibit expression of the target gene, wherein the RNA is a double-stranded molecule with a first ribonucleic acid strand consisting essentially of a ribonucleotide sequence which corresponds to a nucleotide sequence of the target gene and a second ribonucleic acid strand consisting essentially of a ribonucleotide sequence which is complementary to the nucleotide sequence of the target gene. Furthermore, the first and the second ribonucleotide strands are separately complementary strands that hybridize to each other to form the said double-stranded construct, and the double-stranded construct inhibits expression of the target gene.

In using dsRNA in controlling a target insect, one method is to engineer a baculovirus to produce a dsRNA construct in vivo as disclosed in Liu, et al. (U.S. Pat. No. 6,846,482). Salient to Liu is contacting an insect with a recombinant baculovirus wherein a first ribonucleic acid sequence corresponds to at least a portion of at least one gene endogenous to the insect to control the insect. Given the advances made in the field of transfection efficiency and RNA interference, there is a need in the art to utilize RNA interference technology without using a baculovirus as a vector. Such a method would mediate control of a target-pest without depending on variables associated with a baculovirus, such as expression and transfection of dsRNA by the baculovirus.

To utilize RNA interference as a method to regulate gene expression for control, a specific essential gene needs to be targeted. Genes associated with neurohormones represent novel potential targets. One neurohoromone gene family is the pheromone-biosynthesis-activating neuropeptide (PBAN)/pyrokinin gene family. The PBAN/pyrokinin gene produces multiple peptides, each of which are defined by a similar 5-amino-acid C-terminal sequence (FXPRLamide) that is the active core fragment for these peptides as reported in Raina, A. K. and T. G. Kempe (1992). "Structure activity studies of PBAN of *Helicoverpa zea* (Lepidoptera: Noctuidae)." Insect Biochem Mol Biol 22 (3): 221-225. It was subsequently determined that the five C-terminal amino acids, FXPRLamide, represented the minimal sequence required for activity as reported in Raina, A. K. and T. G. Kempe (1992) id.; Fonagy, A., L. Schoofs, et al. (1992). "Functional cross-reactivities of some locusta myotropins and *Bombyx* pheromone biosynthesis activating neuropeptide." J Insect Physiol 38 (9): 651-657; Kuniyoshi, H., H. Nagasawa, et al. (1992). "Cross-activity between pheromone biosynthesis activating neuropeptide (PBAN) and myotropic pyrokinin insect peptides." Biosci Biotechnol Biochem 56 (1): 167-8; and Raina, A. K. and T. G. Kempe (1990). "A pentapeptide of the C-terminal sequence of PBAN with pheromonotropic activity." Insect Biochem 20 (8): 849-851.

Members of the pheromone-biosynthesis-activating neuropeptide (PBAN)/pyrokinin peptide family have been shown to have a variety of functions in insects includes: 1) stimulate pheromone biosynthesis in female moths (Raina et al., 1989); 2) induce melanization in moth larvae (Matsumoto et al., 1990; Altstein et al., 1996); 3) induce embryonic diapause and seasonal polyphenism in moths (Suwan et al., 1994; Uehara et al., 2011); 4) stimulate visceral muscle contraction (Nachman et al., 1986; Predel and Nachman, 2001); 5) accelerate puparium formation in several flies (Zdarek et al., 1997; Verleyen et al., 2004); 6) terminate pupal diapause in heliothine moths (Sun et al., 2003; Xu and Denlinger, 2003).

To date, over 200 PBAN/pyrokinin family peptides including peptides deduced from 40 species PBAN/pyrokinin genes have been identified. While it is one of the largest neuropeptide families in insects, the physiological functions of the PBAN/Pyrokinin peptides are only partially known. As such there is a need in the art to investigative whether the PBAN/Pyrokinin pathway can be used to interfere with essential developmental and/or reproductive functions of the targeted insect pests and result in abnormal development and/or lack of reproduction.

Furthermore there is a need for novel control methods that would interfere with essential developmental and/or reproductive functions of species that do not have the undesirable characteristics of traditional chemical pesticides. To that end, there is a need to develop dsRNA constructs that are engineered to interfere with essential developmental and/or reproductive functions of specific pest insects that would overcome some of the disadvantages of using traditional pesticides.

BRIEF SUMMARY OF THE INVENTION

Disclosed herewith is a method for controlling *Solenopsis invicta*, the method comprising: constructing a double-stranded ribonucleic acid construct that is complementary to a gene that encodes a PBAN/Pyrokinin gene sequence, dissolving the double-stranded ribonucleic acid to form a solution, and contacting an effective amount of said solution to *Solenopsis invicta*, wherein said solution is ingested by *Solenopsis invicta* and RNA interference is induced, resulting in disruption of critical developmental and/or reproductive functions of *Solenopsis invicta*. In an embodiment of the invention, the double-stranded ribonucleic acid is complementary to the nucleotide sequence of SEQ. ID. NO. 1. In another embodiment of the invention the double-stranded ribonucleic acid construct is dissolved in a sucrose solution. In yet another embodiment of the invention the double-stranded ribonucleic acid construct is dissolved with water. In another embodiment of the invention the solution is applied to *Solenopsis invicta* bait material. In yet another embodiment of the invention the bait material contains a phagostimulant. In one embodiment of the invention the solution is applied topically to *Solenopsis invicta*. In another embodiment of the invention, the solution is fed to *Solenopsis invicta* workers. In yet another embodiment of the invention the solution is fed to *Solenopsis invicta* larvae.

Also disclosed herein is a double-stranded ribonucleic acid (dsRNA) for inhibiting the expression of a pheromone-biosynthesis-activating neuropeptide/pyrokynin peptide in a cell, wherein said dsRNA comprises a sense strand comprising a first sequence and an antisense strand comprising a second sequence complementary to SEQ. ID. NO. 2, wherein said first sequence is complementary to said second sequence. In one embodiment of the invention, the double-stranded ribonucleic acid construct is expressed in a plant cell.

Also disclosed herein is a double-stranded ribonucleic acid (dsRNA) for inhibiting the expression of a pheromone-biosynthesis-activating neuropeptide/pyrokynin peptide in a cell, wherein said dsRNA comprises a sense strand comprising a first sequence and an antisense strand comprising a second sequence complementary to SEQ. ID. NO. 3, wherein said first sequence is complementary to said second sequence. In one embodiment of the invention, the double-stranded ribonucleic acid construct is expressed in a plant cell.

BRIEF DESCRIPTION OF THE DRAWINGS

The present invention together with the disclosed embodiments may best be understood from the following detailed description of the drawings, wherein.

BRIEF DESCRIPTION OF THE SEQUENCES

SEQ. ID. NO. 1:
ATGATCGTCACCAGGAATTCCGT-
TAATCGTGCAACTATCGTCTGCATTATGG

CCATGCTGCTCTGCT-
TGGGGTCTCGCGCTTCTGGTGAATACGAATCAAGGGA

AATTGGCTCTAACGGCGGATCGAGT-
GAGAGTAGATCTCCGAGCAACGATTTT

GGTTCCTGTATCGACGGCAAATGTAT-
CAAGCGCACCTCGCAGGATATCGCCA

GCGGCATGTGGTTCGGCCCGCGTTTAG-
GAAAGCGATACAAGTCAGATGAGAA

ACAGGAATTGAGTTCCGAGATCGAGATC-
CTTGCGAACGCGTTAGATGGCGTG

CGTTGGGCGGTCATCACAATTCCG-
GCTAGTGACAAGAGACAGCCTCAATTTA

CTCCGCGTCTGGGACGAGGATCAGGT-
GAGGACCTCTCTTACGGAGACGCATA

CGAAGTCGACGAAGACGACCATCCAT-
TATTCGTGCCCCGTTTAGGACGACGG

CTTCCCTGGATACCATCACCGAGACTCG-
GACGTCAATTACGCAACGTATTAC

GAAAACTATAG is the PBAN/pyrokinin gene cDNA of *Solenopsis invicta*.

SEQ. ID. NO. 2: is a 5' to 3' forming one strand of the dsRNA product referred to as SoiPBAN dsRNA construct.

SEQ. ID. NO. 2:
AUGAUCGUCACCAGGAAUUCCGUUAAUCGUGCAACUAUCGUCUGCAUUAU

GGCCAUGCUGCUCUGCUUGGGGUCUCGCGCUUCUGGUGAAUACGAAUCAA

GGGAAAUUGGCUCUAACGGCGGAUCGAGUGAGAGUAGAUCUCCGAGCAAC

GAUUUUGGUUCCUGUAUCGACGGCAAAUGUAUCAAGCGCACCUCGCAGGA

UAUCGCCAGCGGCAUGUGGUUCGGCCCGCGUUUAGGAAAGCGAUACAAGU

CAGAUGAGAAACAGGAAUUGAGUUCCGAGAUCGAGAUCCUUGCGAACGCG

UUAGAUGGCGUGCGUUGGGCGGUCAUCACAAUUCCGGCUAGUGACAAGAG

ACAGCCUCAAUUUACUCCGCGUCUGGGACGAGGAUCAGGUGAGGACCUCU

CUUACGGAGACGCAUACGAAGUCGACGAAGACGACCAUCCAUUAUUCGUG

CCCCGUUUAGGACGACGGCUUCCCUGGAUACCAUCACCGAGACUCG

SEQ. ID. NO. 3: is a 3' to 5' construct forming one strand of the dsRNA product referred to as SoiPBAN dsRNA construct.

SEQ. ID. NO. 3:
UACUAGCAGUGGUCCUUAAGGCAAUUAGCACGUUGAUAGCAGACGUAAUA

CCGGUACGACGAGACGAACCCCAGAGCGCGAAGACCACUUAUGCUUAGUU

CCCUUUAACCGAGAUUGCCGCCUAGCUCACUCUCAUCUAGAGGCUCGUUG

CUAAAACCAAGGACAUAGCUGCCGUUUACAUAGUUCGCGUGGAGCGUCCU

AUAGCGGUCGCCGUACACCAAGCCGGGCGCAAAUCCUUUCGCUAUGUUCA

GUCUACUCUUUGUCCUUAACUCAAGGCUCUAGCUCUAGGAACGCUUGCGC

AAUCUACCGCACGCAACCCGCCAGUAGUGUUAAGGCCGAUCACUGUUCUC

UGUCGGAGUUAAAUGAGGCGCAGACCCUGCUCCUAGUCCACUCCUGGAGA

GAAUGCCUCUGCGUAUGCUUCAGCUGCUUCUGCUGGUAGGUAAUAAGCAC

GGGGCAAAUCCUGCUGCCGAAGGGACCUAUGGUAGUGGCUCUGAGC

DETAILED DESCRIPTION OF THE INVENTION

Disclosed here are specific insect pest dsRNA constructs that target PBAN/Pyrokinin gene expression. Using dsRNA inhibiting expression of the PBAN/Pyrokinin gene as a means of interfering with critical functions of the PBAN/Pyrokinin gene peptide products, a novel method to develop nucleic acid control for pest management is disclosed.

DEFINITIONS

As used in the specification and claims, the singular form "a", "an" and "the" include plural references unless the context clearly dictates otherwise. For example, the term "a cell" includes a plurality of cells, including mixtures thereof.

The term "gene" refers to a DNA sequence involved in producing a polypeptide or precursor thereof. The polypeptide can be encoded by a full-length coding sequence or by any portion of the coding sequence, such as exon sequences. In one embodiment of the invention, the gene target is a PBAN/Pyrokinin gene of an insect.

The term "pheromone-biosynthesis-activating neuropeptide/pyrokynin peptide" for *Solenopsis invicta*, refer to four gene product peptides comprising: TSQDIASGMWFGPRL (SEQ. ID. NO. 10), QPQFTPRL (SEQ. ID. NO. 11), GSGEDLSYGDAYEVDEDDHPLFVPRL (SEQ. ID. NO. 12), and LPWIPSPRL (SEQ. ID. NO. 13).

The term "oligonucleotide" refers to a molecule comprising a plurality of deoxyribonucleotides or ribonucleotides. Oligonucleotide may be generated in any manner, including chemical synthesis, DNA replication, reverse transcription, polymerase chain reaction, or a combination thereof. The present invention embodies utilizing the oligonucleotide in the form of dsRNA as means of interfering with a critical developmental or reproductive process that leads to control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

The term "double-stranded RNA" or "dsRNA" refers to two substantially complementary strands of ribonucleic acid. "Identity," as used herein, is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M Stockton Press, New York (1991)). Methods commonly employed to determine identity between sequences include, for example, those disclosed in Carillo, H., and Lipman, D., *SIAM J. Applied Math.* (1988) 48:1073. "Substantially identical" as used herein, means there is a very high degree of homology (preferably 100% sequence identity) between the inhibitory dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base pair random mismatches between the RNA and the target gene, provided that the mismatches occur at a distance of at least three nucleotides from the fusion site.

As used herein, "target gene" refers to a section of a DNA strand of a double-stranded DNA that is complementary to a section of a DNA strand, including all transcribed regions, that serves as a matrix for transcription. The target gene is therefore usually the sense strand.

The term "complementary RNA strand" refers to the strand of the dsRNA, which is complementary to an mRNA transcript that is formed during expression of the target gene, or its processing products. "dsRNA" refers to a ribonucleic acid molecule having a duplex structure comprising two complementary and anti-parallel nucleic acid strands. Not all nucleotides of a dsRNA must exhibit Watson-Crick base pairs. The maximum number of base pairs is the number of nucleotides in the shortest strand of the dsRNA.

As used herein, the term "GFP dsRNA" refers to a control dsRNA construct. The green fluorescent protein (GFP) is commonly used as a reporter gene and was originally isolated from jellyfish and widely used as control in prokaryotic and eukaryotic systems.

"Small interfering RNA" or "siRNA" refers to a short double-strand of ribonucleic acid, approximately 18 to 30 nucleotides in length. The term "RNA interference" or "RNAi" refers to a cellular mechanism for the destruction of targeted ribonucleic acid molecules. Under endogenous conditions, RNAi mechanism operates when dsRNA is cleaved to siRNA via an enzyme, DICER. The siRNA is processed to a single strand of anti-sense ribonucleic acid and coupled with a protein complex named RISC. The antisense RNA then targets a complementary gene construct, such as messenger RNA that is cleaved by ribonuclease. While the examples infra discloses constructing dsRNA constructs via enzymatic techniques with the enzyme RNA polymerase, it is contemplated that siRNA can be constructed via RNA oligonucleotide synthesis such as those disclosed in Scaringe, S., Methods Enzymol., 2000, Vol. 317:3 and incorporated herein by reference.

As used herein, "knock-down" is defined as the act of binding an oligonucleotide with a complementary nucleotide sequence of a gene as such that the expression of the gene or mRNA transcript decreases. In an embodiment, knock-down of a PBAN/pyrokinin gene occurs via injection of a dsRNA that can have multiple negative effects on the target insect, such as incomplete metamorphosis to the adult stage and untimely death of the target insect. Evidence of dsRNA having a negative effect on a targeted insect includes incomplete eclosion.

The term "substantially single-stranded" when used in reference to a nucleic acid product means that the product molecule exists primarily as a single strand of nucleic acid in contrast to a double-stranded product which exists as two strands of nucleic acids which are held together by inter-strand base pairing interactions.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

The term "corresponds to" as used herein means a polynucleotide sequence homologous to all or a portion of a reference polynucleotide sequence, or a polypeptide sequence that is identical to a reference polypeptide sequence. In contradistinction, the term "complementary to" is used herein to mean that the complementary sequence is homologous to all or a portion of a reference polynucleotide sequence. For example, the nucleotide sequence "TATAC" corresponds to a reference sequence "TATAC" and is complementary to a reference sequence "GTATA".

An "effective amount" is an amount sufficient to effect desired beneficial or deleterious results. An effective amount can be administered in one or more administrations. In terms of treatment, an "effective amount" is that amount sufficient to make the target pest non-functional by causing an adverse effect on that pest, including (but not limited to) physiological damage to the pest; inhibition or modulation of pest growth; inhibition or modulation of pest reproduction; or death of the pest. In one embodiment of the invention, a dsRNA containing solution is fed to a target insect wherein critical developmental and/or reproductive functions of said insect are disrupted as a result of ingestion.

The term "solvent" includes any liquid that holds another substance in solution. Examples of solvents include but are not limited to water and organic solvents such as acetone, ethanol, dimethyl sulfoxide (DMSO), and dimethylformamide (DMF).

The term "phagostimulant" refers to any substance that will entice the insect to ingest the dsRNA. For insects, suitable phago stimulants include but are not limited to edible oils and fats, vegetable seed meals, meal by-products such as blood, fish meal, syrups, honey, aqueous solutions of sucrose, artificial sweeteners such as sucralose, saccharin, and other artificial sweeteners, peanut butter, cereals, amino acids, and other proteins.

Methods which are well known to those skilled in the art may be used to construct expression vectors containing sequences encoding PBAN/Pyrokinin gene and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) Current Protocols in Molecular Biology, John Wiley & Sons, New York, N.Y.

While the examples provided wherein describe dsRNA constructs cloned from GenBank Accession Nos. FJ223176 (*Solenopsis invicta*), it is contemplated that when read in conjunction with the teaching disclosed herein, the construction of other dsRNA constructs targeting PBAN/pyrokinin gene sequences of other insect orders would be feasible to those skilled the in the art. For example, including but not limited to the PBAN/pyrokinin gene/amino acid sequences disclosed in Table 1, it is contemplated that a dsRNA construct targeting the species disclosed in Table 1 of known PBAN/pyrokinin genes would control that respective insect. Additionally it is contemplated that a single dsRNA construct would be effective in controlling a plurality of insect species.

TABLE 1

| Insect Order | Species | GenBank Accession # |
|---|---|---|
| Lepidoptera | Helicoverpa zea | U08109 |
| | Helicoverpa assulta | U96761/AY052417 |
| | Helicoverpa armigera | AY043222 |
| | Heliothis virescens | AY173075 |
| | Agrotis ipsilon | AJ009674 |
| | Mamestra brassicae | AF044079 |
| | Spodoptera littoralis | AF401480 |
| | Spodoptera exigua | AY628764 |
| | Pseudaletia separate | P25271 (amino acid sequence only) |
| | Clostera anastomosis | AY786305 |
| | Orgyia thyellina | AB259122 |
| | Lymantria dispar | AAB32665 (amino acid sequence only) |
| | Antheraea pernyi | AY445658 |
| | Samia cynthia ricini | AY286544 |
| | Manduca sexta | AY172672 |
| | Bombyx mori | NM_001043856 |
| | Bombyx mandarina | J. Sericultural Science of Japan, 68: 373-379 |
| | Ascotis selenaria cretacea | AB308061 |
| | Adoxophyes. sp | AF395670 |
| | Plutella xylostella | AY904342 |
| Diptera | Drosophila melanogaster | AY047528 |
| | Drosophila mauritiana | EF386943 |
| | Drosophila sechellia | EF386942 |
| | Drosophila simulans | EF386941 |
| | Aedes aegypti | XM_001650839/ XM_001662162 |
| | Culex quinquefasciatus | XM_001847366 |
| | Anopheles gambiae | XM_307885 |
| Coleoptera | Tribolium castaneum | EFA11568 |
| Hymenoptera | Apis melifera | NM_001110712 |
| | Nasonia vitripennis | NM_001167725 |
| | Solenopsis invicta | FJ223176 |
| | Solenopsis richteri | GQ872200 |
| | Solenopsis geminata | GQ872197 |
| | Solenopsis pergandei | GQ872198 |
| | Solenopsis carolinenesis | GQ872199 |
| | Harpegnathos saltator | GL445232 |
| | Camponotus floridanus | GL439118 |
| | Linepithema humile | Unpublished data |
| Hemiptera | Acyrthosiphon pisum (pea aphid) | Gene ID: ACYPIG135047 |
| | Rhodnius prolixus | GU230851 |

EXAMPLE 1

Constructing dsRNA Construct for *Solenopsis invicta*

Cloning and Sequencing of Soi-PBAN Gene from *Solenopsis invicta*

A mRNA was isolated from the dissected brain-subesophageal ganglion (Br-SGs) from *Solenopsis invicta* female alates by Micro Fast mRNA purification kit (Invitrogen), and used to synthesize cDNA with the GeneRacer cDNA synthesis kit (Invitrogen). Cloning the full length Soi-PBAN gene (GenBank accession number, FJ223176) was carried out using Generacer kit (Invitrogen) as described by the manufacturer. The $1^{st}$ strand cDNA was used to amplify the full length of Soi-PBAN gene using primer set: sense primer, 5'-ATCGCCAGCGGCATGTGGTTCGGCC-3 (SEQ. ID. NO. 4) for 3'-RACE and antisense primer, 5'-GCAC-GAATAATGGATGGTCGTCTTC-3' (SEQ. ID. NO. 5) by PCR amplification. The PCR was performed with the following temperature program: 5 cycles at 95° C. for 30 s, 67° C. for 30 s, and 72° C. for 1 min, 5 cycles at 95° C. for 30 s, 62° C. for 30 s, and 72° C. for 1 min, and 30 cycles at 95° C. for 30 s, 55° C. for 30 s, and 72° C. for 1 min. The PCR product was gel purified and cloned using TOPO TA cloning kit (Invitrogen) and sequenced. The obtained full-length sequence information was aligned and sequences compared with our partial sequence using DNA analysis software.

Construction of Soi-PBAN dsRNA Construct and GFP dsRNA as Control

To construct Soi-PBAN dsRNA, the full length of Soi-PBAN cDNA (531-bp) obtained above was used by specific 5'-T7-appended PCR primers 5'-TAATACGAC TCACTAT-AGGGA CCGTCGACAACCGACTTAC-3' (SEQ. ID. NO. 6) and 5'-AATACGACTCACTATAGGG GACTCTCAA-GAGGTGGT GGC-3' (SEQ. ID. NO. 7) to amplify a 496-bp Soi-PBAN DNA fragment, which serves as the template for dsRNA synthesis using the MEGAscript RNA kit (Ambion). For a negative control, a green fluorescence protein (GFP) dsRNA was purchased from Ambion or was synthesized from a 546-bp GFP DNA template amplified by these primers 5'-TAATACGACTCACTATAGGGACGTAAA CGGC-CACA AGTTC-3' (SEQ. ID. NO. 8) and 5'-TAATACGACT-CACTATAGGGTGCTCAGGTAGTGGTTGTCG-3' (SEQ. ID. NO. 9) using the same kit as above. The length of Soi-PBAN dsRNA (SEQ. ID. NO. 2 and SEQ. ID. NO. 3) was constructed from the full length of Soi-PBAN cDNA, 531-bp (SEQ. ID. NO. 1).

EXAMPLE 2

Injection Soi-PBAN dsRNA in Adult *Solenopsis invicta* Bioassay

Figure 1:
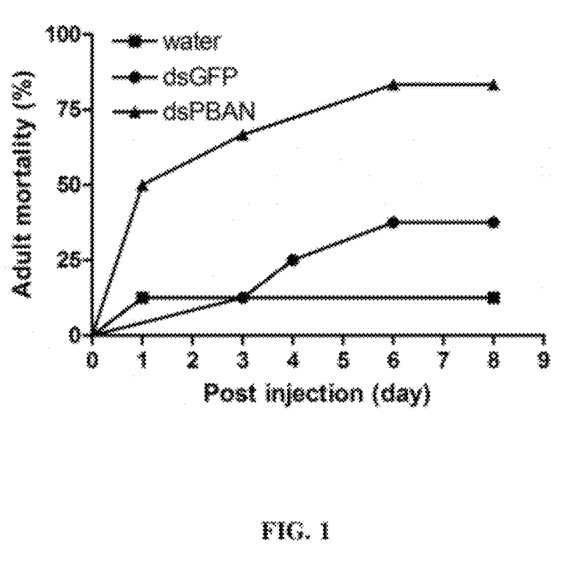
FIG. 1 is a graph depicting the percentage of mortality in adult *Solenopsis invicta* workers after being injected with Soi-PBAN dsRNA (20 ηg), water control, or dsGFP (20 ηg) into hemocoel of major workers. The data was analyzed by Kaplan-Meier survival curve comparison (PBAN vs. GFP & water, p=0.044 & 0.023, respectively, n≥7).

The dsRNA construct comprising the complementary strands of SEQ. ID. NO. 2 and SEQ. ID. NO. 3 was injected into the hemocoel of *Solenopsis invicta* workers using a Nanoliter 2000™ System using pulled borosilicate needles (World Precision Instruments). Specifically 20 ng of Soi-PBAN dsRNA was injected into 25 workers and observed for seven days. For a control, 20 ng of GFP dsRNA as disclosed in Example 1 was injected into 25 workers. 50 nl distilled water was also injected into 25 workers as an additional control. As depicted in FIG. 1, it was observed that 83.3% of *Solenopsis invicta* workers resulted in mortality as compared to 15.6% mortality and 12.5% mortality of dsRNA GFP and distilled water controls, respectively.

EXAMPLE 3

Injection Soi-PBAN dsRNA in *Solenopsis invicta* Pupae Bioassay

Figure 2:
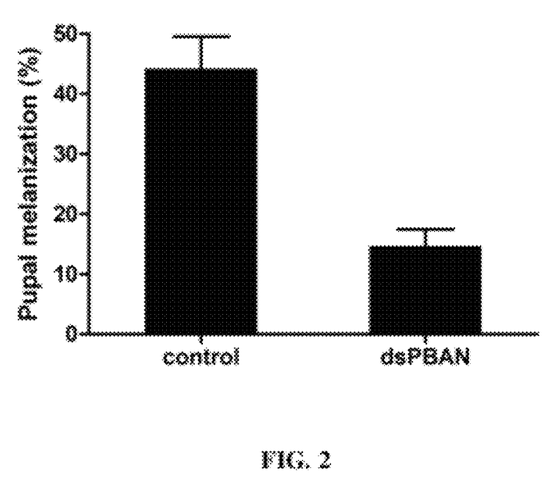
FIG. 2 is a graph depicting the percentage of *Solenopsis invicta* female pupae having cuticle melanization and pupal mortality after being injected with either Soi-PBAN dsRNA, or the control groups of water and GFP and observed for 8 days. The mean+s.e.m. (n≥25) are shown. Bars with different letters are significantly different (unpaired t-test, two-tailed, P=0.013).
Figure 3:
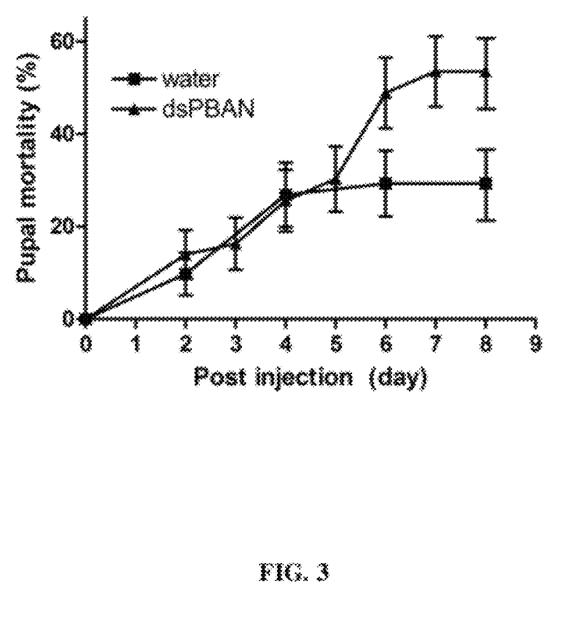
FIG. 3 is a graph depicting the mortality of the fire ant pupae after SoiPBAN dsRNA injection. Young female alate pupae, 24-48 h-old, were injected with 20 ng SoiPBAN dsRNA or water (50 nL/pupa). Cumulative pupae mortality was recorded for 8 days until adult emergence. SoiPBAN dsRNA treatment and water control were repeated three times (×3). Data was analyzed by Kaplan-Meier survival curve comparison (P=0.029, n≥25).

The dsRNA construct comprising the complementary strands of SEQ. ID. NO. 2 and SEQ. ID. NO. 3 was injected into female alate pupae *Solenopsis invicta* workers. Specifically 20 ng of Soi-PBAN dsRNA was injected into 25 pupae and observed for eight to ten days during in which adult emergence was expected. For a control, 20 ng of GFP dsRNA as disclosed in example 1 was injected into 25 female alate pupae. 50 mL of distilled water was also injected into 25 female alate pupae as an additional control. The pupae were then observed for mortality and cuticle melanization as visualized as tanning of the said cuticle. Pupa melaniation observations are recorded in FIG. 2. As depicted in FIG. 3, it was observed that 86.5% of *Solenopsis invicta* pupae resulted in mortality as compared to 27.0% mortality and 41.7% mortality of dsRNA GFP and distilled water, respectively. Additionally, melanization occurred in 69.0% of *Solenopsis invicta* pupae as compared to 30.0% and 30.0% melanization of dsRNA GFP and distilled water, respectively.

EXAMPLE 4

Soi-PBAN dsRNA *Solenopsis invicta* Sucrose Feeding Bioassay

Figure 4:
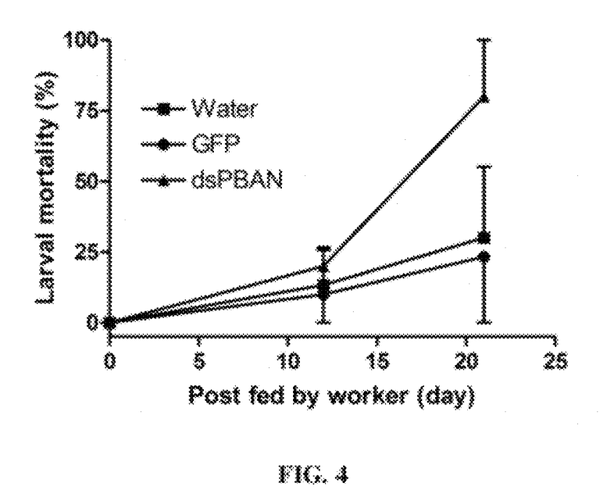
FIG. 4 is a graph depicting mortality of fire ant worker larvae. Nurse workers were fed SoiPBAN dsRNA (1 μg/μL), GFP dsRNA (1 μg/μL), or an aqueous 10% sucrose solution. Accumulated mortality was recorded 12- and 21-days post treatment. The experiment was repeated three times. Data was analyzed by Kaplan-Meier survival curve comparison (PBAN vs. GFP & water, p=0.016 & 0.041, respectively, n≥10). Means values + or − s.e.m. are shown.

The dsRNA construct comprising the complementary strands of SEQ. ID. NO. 2 and SEQ. ID. NO. 3 at (1 µg/µL), GFP dsRNA (1 µg/µL) dissolved in 10% sucrose solution, or an aqueous 10% sucrose solution (wt./vol.) and fed ad libitum for a period of 14 days via a capillary tube to six *Solenopsis invicta* workers that were nursing ten $4^{th}$ instar larvae. Following the initial 14 day feeding period, the workers were then feed only 10% sucrose solution without dsRNA and observed for 21 days. For a control, a 10% sucrose solution was fed to workers without the dsRNA construct and observed over the 21 days. As depicted in FIG. 4, it was observed that 80.0% of *Solenopsis invicta* larvae fed the dsRNA construct resulted in mortality as compared to 30.0% mortality in the control group after 21 days.

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. An isolated double-stranded ribonucleic acid (dsRNA) for inhibiting the expression of a pheromone-biosynthesis-activating neuropeptide/pyrokynin peptide in a cell consisting essentially of sense strand SEQ. ID. NO. 2 with the sense strand being complementary to an antisense strand.

2. The isolated double-stranded ribonucleic acid of claim 1 wherein the double-stranded ribonucleic acid is expressed in a transgenic plant cell.

3. An isolated double-stranded ribonucleic acid (dsRNA) for inhibiting the expression of a pheromone-biosynthesis-activating neuropeptide/pyrokynin peptide in a cell consisting essentially of sense strand SEQ. ID. NO. 3 with the sense strand being complementary to an antisense strand.

4. The isolated double-stranded ribonucleic acid of claim 3 wherein the double-stranded ribonucleic acid is expressed in a transgenic plant cell.

5. A method for controlling *Solenopsis invicta*, the method comprising: constructing a double-stranded ribonucleic acid construct that is complementary to a gene that encodes a PBAN/Pyrokinin gene sequence consisting essentially of SEQ. ID. NO. 2 and 3, dissolving the double-stranded ribonucleic acid to form a solution, and contacting an effective amount of said solution to *Solenopsis invicta*, wherein said solution is ingested by *Solenopsis invicta* and RNA interference is induced, resulting in disruption of critical developmental and/or reproductive functions of *Solenopsis invicta*.

6. The method of claim 5, wherein the double-stranded ribonucleic acid construct is dissolved in a sucrose solution.

7. The method of claim 5, wherein the double-stranded ribonucleic acid construct is dissolved in water.

8. The method of claim 5, wherein the solution is applied to *Solenopsis invicta* bait material.

9. The method of claim 8, wherein the bait material contains a phagostimulant.

10. The method of claim 5, wherein the solution is applied topically to *Solenopsis invicta*.

11. The method of claim 5, wherein the solution is fed to *Solenopsis invicta* workers.

12. The method of claim 5, wherein the solution is fed to *Solenopsis invicta* larvae.

13. The *Solenopsis invicta* control solution constructed by the method of claim 5.

14. The method of claim 5, wherein the double-stranded ribonucleic acid construct is expressed in a transgenic plant.

15. The method of claim 14, wherein the plant is a graminoid.

16. The isolated double-stranded ribonucleic acid (dsRNA) of claim 1 wherein the dsRNA is in solution.

17. The isolated double-stranded ribonucleic acid (dsRNA) of claim 3 wherein the dsRNA is in solution.

\* \* \* \* \*

SEQUENCE LISTING

<160> NUMBER OF SEQ ID NOS: 13

<210> SEQ ID NO 1
<211> LENGTH: 531
<212> TYPE: DNA
<213> ORGANISM: Solenopsis invicta

<400> SEQUENCE: 1

```
atgatcgtca ccaggaattc cgttaatcgt gcaactatcg tctgcattat ggccatgctg      60
ctctgcttgg ggtctcgcgc ttctggtgaa tacgaatcaa gggaaattgg ctctaacggc     120
ggatcgagtg agagtagatc tccgagcaac gattttggtt cctgtatcga cggcaaatgt     180
atcaagcgca cctcgcagga tatcgccagc ggcatgtggt tcggcccgcg tttaggaaag     240
cgatacaagt cagatgagaa acaggaattg agttccgaga tcgagatcct tgcgaacgcg     300
ttagatggcg tgcgttgggc ggtcatcaca attccggcta gtgacaagag acagcctcaa     360
tttactccgc gtctgggacg aggatcaggt gaggacctct cttacggaga cgcatacgaa     420
gtcgacgaag acgaccatcc attattcgtg ccccgtttag gacgacggct tccctggata     480
ccatcaccga gactcggacg tcaattacgc aacgtattac gaaaactata g              531
```

<210> SEQ ID NO 2
<211> LENGTH: 496
<212> TYPE: RNA
<213> ORGANISM: Solenopsis invicta

<400> SEQUENCE: 2

```
augaucguca ccaggaauuc cguuaaucgu gcaacuaucg ucugcauuau ggccaugcug      60
cucugcuugg ggucucgcgc uucuggugaa uacgaaucaa gggaaauugg cucuaacggc     120
```

```
ggaucgagug agaguagauc uccgagcaac gauuuugguu ccuguaucga cggcaaaugu    180
aucaagcgca ccucgcagga uaucgccagc ggcauguggu ucggcccgcg uuuaggaaag    240
cgauacaagu cagaugagaa acaggaauug aguuccgaga ucgagauccu ugcgaacgcg    300
uuagauggcg ugcguuggcgc ggucaucaca auuccggcua gugacaagag acagccucaa   360
```
uuagauggcg ugcguuggc ggucaucaca auuccggcua gugacaagag acagccucaa    360
uuuacuccgc gucugggacg aggaucaggu gaggaccucu cuuacggaga cgcauacgaa    420
gucgacgaag acgaccaucc auuauucgug ccccguuuag gacgacggcu ucccuggaua    480
ccaucaccga gacucg                                                   496

<210> SEQ ID NO 3
<211> LENGTH: 496
<212> TYPE: RNA
<213> ORGANISM: Solenopsis invicta

<400> SEQUENCE: 3
uacuagcagu gguccuuaag gcaauuagca cguugauagc agacguaaua ccgguacgac     60
gagacgaacc ccagagcgcg aagaccacuu augcuuaguu cccuuuaacc gagauugccg    120
ccuagcucac ucucaucuag aggcucguug cuaaaaccaa ggacauagcu gccguuuaca    180
uaguucgcgu ggagcguccu auagcggucg ccguacacca agccgggcgc aaauccuuuc    240
gcuauguuca gucuacucuu uguccuuaac ucaaggcucu agcucuagga acgcuugcgc    300
aaucuaccgc acgcaacccg ccaguagugu uaaggccgau cacuguucuc ugucggaguu    360
aaaugaggcg cagacccugc uccuagucca cuccuggaga gaaugccucu gcguaugcuu    420
cagcugcuuc ugcugguagg uaauaagcac ggggcaaauc cugcugccga agggaccuau    480
gguaguggcu cugagc                                                   496

<210> SEQ ID NO 4
<211> LENGTH: 25
<212> TYPE: DNA
<213> ORGANISM: Solenopsis invicta

<400> SEQUENCE: 4
atcgccagcg gcatgtggtt cggcc                                          25

<210> SEQ ID NO 5
<211> LENGTH: 25
<212> TYPE: DNA
<213> ORGANISM: Solenopsis invicta

<400> SEQUENCE: 5
gcacgaataa tggatggtcg tcttc                                          25

<210> SEQ ID NO 6
<211> LENGTH: 40
<212> TYPE: DNA
<213> ORGANISM: Solenopsis invicta

<400> SEQUENCE: 6
taatacgact cactataggg accgtcgaca accgacttac                          40

<210> SEQ ID NO 7
<211> LENGTH: 39
<212> TYPE: DNA
<213> ORGANISM: Solenopsis invicta

<400> SEQUENCE: 7
aatacgactc actagggg actctcaaga ggtggtggc                             39

```
<210> SEQ ID NO 8
<211> LENGTH: 40
<212> TYPE: DNA
<213> ORGANISM: Solenopsis invicta

<400> SEQUENCE: 8
taatacgact cactataggg acgtaaacgg ccacaagttc                    40

<210> SEQ ID NO 9
<211> LENGTH: 40
<212> TYPE: DNA
<213> ORGANISM: Solenopsis invicta

<400> SEQUENCE: 9
taatacgact cactataggg tgctcaggta gtggttgtcg                    40

<210> SEQ ID NO 10
<211> LENGTH: 15
<212> TYPE: PRT
<213> ORGANISM: Solenopsis invicta

<400> SEQUENCE: 10

Thr Ser Gln Asp Ile Ala Ser Gly Met Trp Phe Gly Pro Arg Leu
1               5                   10                  15

<210> SEQ ID NO 11
<211> LENGTH: 8
<212> TYPE: PRT
<213> ORGANISM: Solenopsis invicta

<400> SEQUENCE: 11

Gln Pro Gln Phe Thr Pro Arg Leu
1               5

<210> SEQ ID NO 12
<211> LENGTH: 26
<212> TYPE: PRT
<213> ORGANISM: Solenopsis invicta

<400> SEQUENCE: 12

Gly Ser Gly Glu Asp Leu Ser Tyr Gly Asp Ala Tyr Glu Val Asp Glu
1               5                   10                  15

Asp Asp His Pro Leu Phe Val Pro Arg Leu
            20                  25

<210> SEQ ID NO 13
<211> LENGTH: 9
<212> TYPE: PRT
<213> ORGANISM: Solenopsis invicta

<400> SEQUENCE: 13

Leu Pro Trp Ile Pro Ser Pro Arg Leu
1               5
```